United States Patent
Green et al.

(10) Patent No.: US 7,327,863 B1
(45) Date of Patent: Feb. 5, 2008

(54) STAND-UP PATIENT HANDLING SYSTEM CONTROL KIOSK AND CONTROLLER

(75) Inventors: Charles A. Green, Holbrook, NY (US);
Mark Gelbien, Levittown, NY (US);
Joseph Citro, Hauppauge, NY (US)

(73) Assignee: Fonar Corporation, Melville, NY (US)

( * ) Notice: Subject to any disclaimer, the term of this patent is extended or adjusted under 35 U.S.C. 154(b) by 642 days.

(21) Appl. No.: 10/301,187

(22) Filed: Nov. 21, 2002

Related U.S. Application Data

(60) Provisional application No. 60/373,964, filed on Apr. 19, 2002, provisional application No. 60/332,103, filed on Nov. 21, 2001.

(51) Int. Cl.
*G06K 9/00* (2006.01)
(52) U.S. Cl. .................. 382/128; 382/151; 378/15
(58) Field of Classification Search ........ 382/128–133, 382/153, 156, 168, 203, 207, 254, 260, 274, 382/276, 289, 296, 297, 305; 307/66; 434/262; 324/318; 600/410, 564; 312/258; 235/383; 378/15
See application file for complete search history.

(56) References Cited

U.S. PATENT DOCUMENTS

| | | | |
|---|---|---|---|
| 3,789,832 A | 2/1974 | Damadian | |
| 4,629,989 A * | 12/1986 | Riehl et al. .................. 324/318 |
| 4,770,182 A * | 9/1988 | Damadian et al. .......... 600/410 |
| 4,968,937 A | 11/1990 | Akgun | |
| 5,008,624 A | 4/1991 | Yoshida | |
| 5,065,761 A | 11/1991 | Pell | |
| 5,289,374 A | 2/1994 | Doi et al. | |
| 5,735,278 A | 4/1998 | Hoult et al. | |
| 5,800,178 A * | 9/1998 | Gillio ......................... 434/262 |
| 5,808,376 A * | 9/1998 | Gordon et al. ................. 307/66 |
| 5,878,746 A | 3/1999 | Lemelson et al. | |
| 6,023,165 A * | 2/2000 | Damadian et al. .......... 324/318 |
| 6,198,285 B1 * | 3/2001 | Kormos et al. ............. 324/318 |
| 6,289,326 B1 * | 9/2001 | LaFleur ...................... 312/258 |
| 6,414,490 B1 | 7/2002 | Damadian et al. | |
| 6,471,659 B2 * | 10/2002 | Eggers et al. ............... 600/564 |
| 6,892,941 B2 * | 5/2005 | Rosenblum ................. 235/383 |

OTHER PUBLICATIONS

U.S. Appl. No. 09/718,946, filed Nov. 22, 2000.
U.S. Appl. No. 08/978,084, filed Nov. 27, 1997, (now abandoned).

* cited by examiner

*Primary Examiner*—Seyed Azarian
(74) *Attorney, Agent, or Firm*—Lerner, David, Littenberg, Krumholz & Mentlik, LLP (57) ABSTRACT

Apparatus and methods for magnetic resonance imaging are provided. The apparatus desirably comprises an MRI magnet subsystem and a control kiosk spatially separate from the MRI subsystem. The control kiosk may be advantageously located inside or outside the shielded room housing the MRI subsystem. The method comprises the steps of providing a control kiosk spatially separate from the MRI subsystem and positioning and viewing a patient within a patient-receiving space of the main subsystem. In accordance with another aspect of the invention, a magnetic resonance imaging apparatus comprising a relay having a power input and power output connected to a power supply of an actuator control unit is provided.

20 Claims, 10 Drawing Sheets

STAND-UP PATIENT HANDLING SYSTEM CONTROL KIOSK AND CONTROLLER

CROSS-REFERENCE TO RELATED APPLICATIONS

The present application claims the benefit of U.S. Provisional Application Ser. No. 60/332,103, filed Nov. 21, 2001 and entitled "Stand-Up Patient Handling System Control Kiosk," and U.S. Provisional Application Ser. No. 60/373,964, filed Apr. 19, 2002 and entitled "Patient Handling System Control Kiosk and Controller," the disclosures of which are incorporated in entirety by reference herein.

BACKGROUND OF THE INVENTION

The present invention relates to magnetic resonance imaging apparatus and procedures. In magnetic resonance imaging, an object to be imaged as, for example, a body of a human subject is exposed to a strong, substantially constant static magnetic field. Radio frequency excitation energy is applied to the body, and this energy causes the spin vectors of certain atomic nuclei within the body to rotate or "precess" around axes parallel to the direction of the static magnetic field. The precessing atomic nuclei emit weak radio frequency signals, referred to herein as magnetic resonance signals. Different tissues produce different signal characteristics. Tissue relaxation times are a major factor in determining signal strength. In addition, tissues having a high density of certain nuclei will produce stronger signals than tissues having a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Several factors impose significant physical constraints in positioning of patients and ancillary equipment in MRI imaging. Many MRI systems use solenoidal superconducting coils to provide the static magnetic field arranged so that the patient is disposed within a small tube running through the center of the coils. The coil and tube typically extend along a horizontal axis, so that the long axis or head-to-toe axis of the patient's body must be in a horizontal position during the procedure. Moreover, equipment of this type provides a claustrophobic environment for the patient. Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns which are located outside the patient-receiving area and extend vertically. A magnetic field is provided by permanent magnets or electromagnetic coils (superconductive or resistive) associated with the frame. A magnet of this type can be designed to provide a more open environment for the patient. However, it is still generally required for the patient to lie with his or her long axis horizontal.

Recently, ferromagnetic frame magnets having horizontal pole axes have been developed. As disclosed, for example, in commonly assigned U.S. patent application Ser. No. 08/978,084, filed on Nov. 25, 1997, and U.S. Pat. No. 6,414,490, the disclosures of which are incorporated by reference herein, and in copending, commonly assigned U.S. patent application Ser. No. 09/718,946, filed on Nov. 22, 2000, the disclosure of which is also incorporated by reference herein, a magnet having poles spaced apart from one another along a horizontal axis provides a horizontally oriented magnetic field within a patient-receiving gap between the poles. Such a magnet can be used with a patient positioning device including elevation and tilt mechanisms to provide extraordinary versatility in patient positioning. For example, where the patient positioning device includes a bed or similar device for supporting the patient in a supine or recumbent position, the bed can be tilted and/or elevated so as to image the patient in essentially any position between a fully standing position and a fully supine or fully recumbent position, and can be elevated so that essentially any portion of the patient's anatomy is disposed within the gap in an optimum position for imaging. As further disclosed in the aforesaid applications, the patient positioning device may include additional elements such as a platform projecting from the bed to support the patient when the bed is tilted towards a standing orientation. Still other patient supporting devices can be used in place of a bed in a system of this type. Thus, magnets of this type provide extraordinary versatility in imaging.

Figure 1:
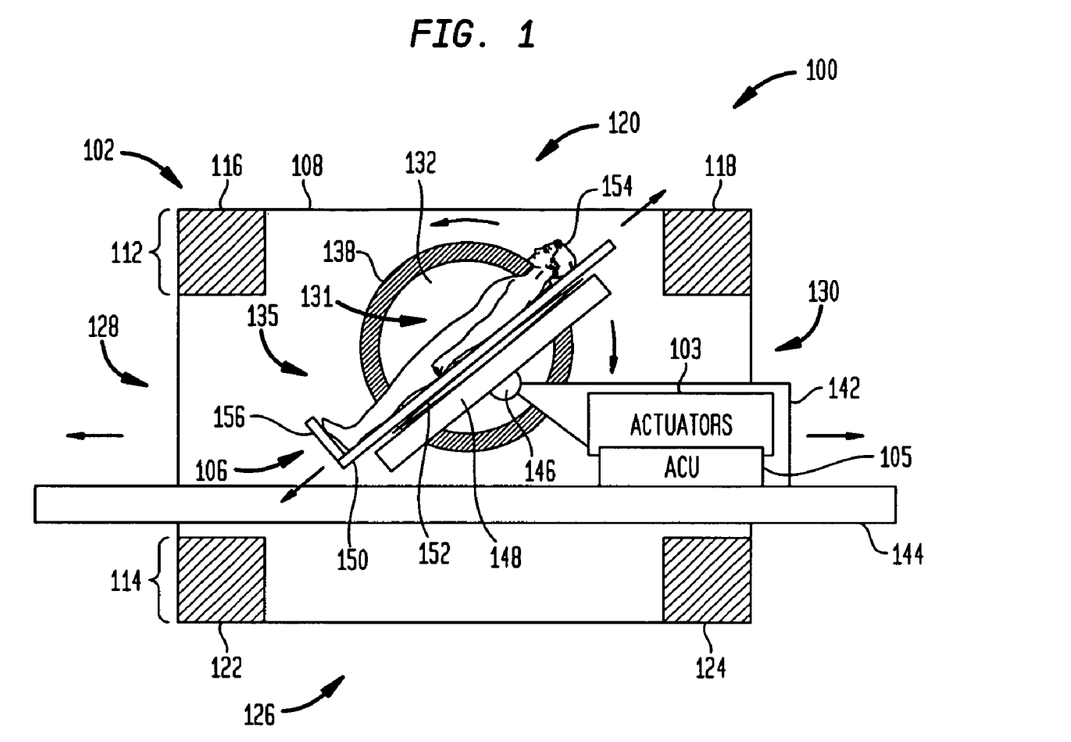
FIG. 1 is a diagrammatic sectional view of a MRI main subsystem with a stand-up patient handling system with certain portions removed for clarity of illustration.

FIG. 1 of the current application shows a sectional view of an MRI magnet subsystem 100. MRI magnet subsystem 100 includes a magnet having a ferromagnetic frame 102, a flux generating means 104 as is described in further detail below, and a patient handling system 106. The ferromagnetic frame 102 includes a first side wall 108 and a second side wall 110. The side walls 108 and 110 extend vertically. For purposes of clarity, FIG. 1 does not show the second side wall 110 or any of its associated structures (see FIG. 5). The ferromagnetic frame 102 also includes a top flux return structure 112 and a bottom flux return structure 114. The top flux return structure 112 may include two columns 116 and 118. Between these two columns, a top opening 120 is defined. Similarly, the bottom flux return structure 114 may include two columns 122 and 124 that together define a bottom opening 126. Thus, the side walls 108 and 110 and the flux return members 112 and 114 form a rectilinear structure, with the top flux return structure 112 constituting the top wall of the rectilinear structure, the bottom flux return structure 114 constituting the bottom wall of the rectilinear structure and the side walls 108 and 110 forming the side walls of the rectilinear structure. The frame 102 of the rectilinear structure defines a front patient opening 128 on one side of the frame 102 and a similar back patient opening 130 on the opposite side of the frame 102. The ferromagnetic frame 102 further includes a first magnetic pole 132 and a second magnetic pole 134. The first magnetic pole 132 extends from the first side wall 108 towards the second side wall 110 and the second magnetic pole 134 extends from the second side wall 110 towards the first side wall 108. Magnetic poles 132 and 134 are generally cylindrical and are coaxial with one another on a common horizontal polar axis 136. Between the magnetic poles 132 and 134 is a gap 131, also referred to as the patient-receiving space, of the magnet. The gap or patient-receiving space 131 is accessed by the front patient opening 128, the back patient opening 130, the top opening 120 or the bottom opening 126.

The flux generating means 104 includes a first electromagnetic coil assembly 138 which surrounds the first magnetic pole 132, and a second electromagnet coil assembly 140, which surrounds the second magnetic pole 134. As previously noted, these electromagnetic coil assemblies 138 and 140 may be either resistive or superconductive.

The patient handling system 106 is capable of three degrees or axes of motion. The patient handling system 106 may be termed a stand-up patient handling system, although the patient handling system 106 is not limited to standing position applications. The patient handling system 106 includes a carriage 142 mounted on rails 144. The carriage 142 may move linearly back and forth along the rails 144. The rails 144 typically do not block the bottom open space 126.

A generally horizontal pivot axis 146 is mounted on carriage 142. An elevator frame 148 is mounted to the pivot axis 146. The carriage 142 is operable to rotate the elevator frame 148 about the pivot axis 146. A patient support 150 is mounted on the elevator frame 148. The patient support 150 may be moved linearly along the elevator frame 148 by an actuator 152. Thus, a patient 154 can be positioned with a total of three degrees of freedom, or along three axes of movement or motion. Specifically, the patient handling system 106 can move a patient 154 in two linear directions and also rotate patient 154 around an axis. The solid black arrows of FIG. 1 show the three axes of movement possible with the patient handling system 106. Note that often the rails 108 are mounted such that portions of patient 154 may be positioned below the rails through bottom open space 126.

Often, a foot rest 156 may be used in order to support a patient in a standing position. Given the wide variety of positions possible with the patient handling system 108, many other such supports may be implemented, such as chair seats or straps.

The patient handling system 106 incorporates one or more actuators 103 and an actuation control unit 105. Actuators 103 may be conventional electrical, electromechanical, pneumatic, hydraulic or other devices capable of imparting the desired motion to the elements of the patient handling system. For example, the actuators may include elements such as conventional stepper motors or other conventional electric motors linked to the elements of the patient handling system 106. The actuator control unit 105 may incorporate a conventional programmable controller, microprocessor, or computer with appropriate input and output interfaces. As further discussed below, the actuation control unit 105 is linked to a control computer and to the manual controls which regulate the patient handling system. The actuation control unit may be mounted in proximity to the actuators 103 as, for example, on carriage 142.

Figure 2A:
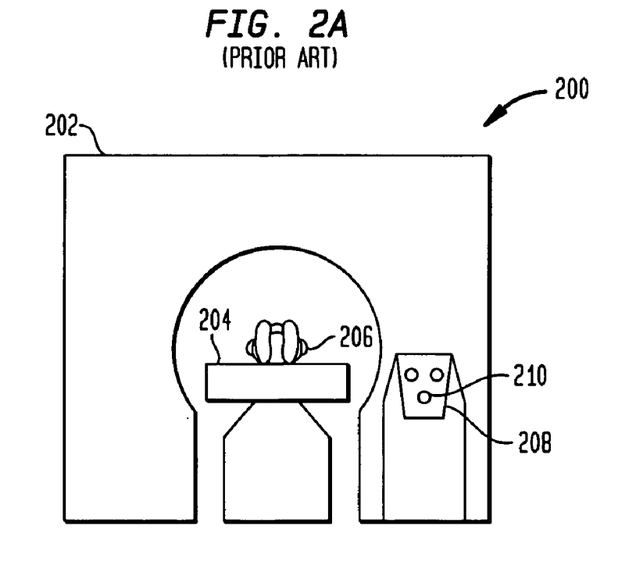
FIGS. 2A and 2B are diagrammatic frontal and side elevation views of an older MRI apparatus.
Figure 2B:
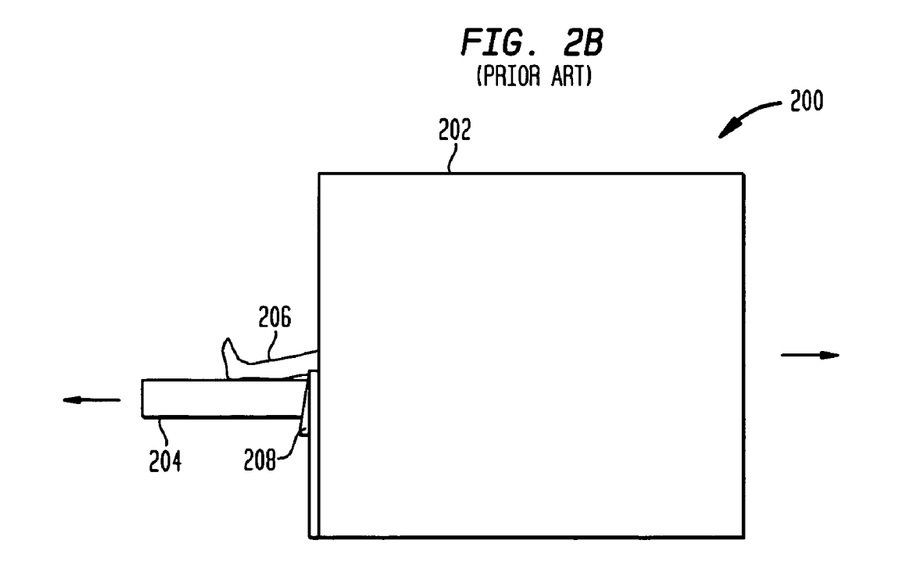

The MRI magnet subsystem 100 with patient handling system 106 can be contrasted with an older MRI system such as shown in FIG. 2. Older MRI apparatus 200 has a magnet canopy 202 and a bed 204 on which the patient 206 lies recumbent. The bed 204 is typically capable only of linear motion to the left and right in the orientation of FIG. 2. This linear motion is restricted to a horizontal plane. Thus, many of the advantages of the patient handling system as discussed in the aforementioned applications are unavailable. A control panel 208 with simple controls 210 may be mounted directly to the magnetic canopy 202. Alternatively, the control panel 208 may be mounted directly to the bed 204.

The greatly increased number of options for positioning a patient available with the patient handling system 106 make the ability to observe the patient 154 during positioning a necessity for operating the patient handling system 106 safely and effectively. For example, it is possible that the patient handling system 106 could place the patient 154 in a potentially undesirable or unsafe position within the frame. Furthermore, the simple controls 210 are not sufficient to control a more complicated patient handling system. It is, thus, desirable to have an easy to use control panel capable of controlling a stand-up patient handling system.

SUMMARY OF THE INVENTION

One aspect of the present invention provides an apparatus for magnetic resonance imaging. The apparatus according to this aspect of the present invention desirably includes an MRI magnet subsystem and a control kiosk spatially separate from the MRI subsystem. The apparatus further desirably includes a pair of magnetic poles and a patient handling system capable of three degrees of freedom or axes of motion between said pair of magnetic poles.

Another aspect of the present invention provides a control kiosk spatially separate from the magnetic resonance imaging apparatus. The control kiosk includes a support structure with a floor end and a top end, and a control housing attached to the top end of the support structure.

Another aspect of the present invention provides a method for operating a magnetic resonance imaging apparatus. The magnetic resonance imaging apparatus includes a stand-up patient handling system. The method includes providing a control kiosk spatially separate from the remainder of said magnetic resonance imaging apparatus; loading a patient into said stand-up patient handling system; positioning the patient by moving said stand-up patient operating system; and viewing said position of the patient.

Apparatus according to yet another aspect of the invention includes a magnet defining a patient-receiving space and a patient handling system incorporating one or more actuators and an actuation control unit which is at least partially operated by electricity as, for example, an electronic programmable controller, an electromechanical control unit, or an electropneumatic or electrohydraulic controller. The actuation control unit has a power supply connection, a power control output, and one or more actuator control outputs connected to the one or more actuators. Typically, the actuators and the actuation control unit are arranged so that in at least some operating conditions of the patient handling system, the actuation control unit is disposed in or adjacent the patient-receiving space. The apparatus according to this aspect of the invention also includes a relay having a line power input, a power output connected to the power supply connection of the actuator control unit, and a control input connected to the power control output of the actuation control unit. The relay is arranged to connect the line power input to the power output, and hence to the power supply connection of the actuation control unit in response to a signal applied to the control input. Preferably, the relay is arranged to maintain this connection only while a signal is applied to its control input. The relay may be a conventional electromechanical relay or a solid state device such as a device incorporating a power transistor, a field effect transistor, thyristor or other solid-state control element.

Apparatus according to this aspect of the invention desirably also includes an auxiliary control power source such as a battery or an auxiliary line connection. A switch, most preferably a manually-operable momentary switch, is connected between the auxiliary control power source and the control input of the relay. For example, in a structure including a kiosk as discussed above, the switch can be mounted on the kiosk. Using this arrangement, the relay can be actuated to supply power to the actuation control unit by operating the switch to supply a signal from the auxiliary control power source to the control input of the relay, whereupon the relay supplies power to the actuation control unit. Once the actuation control unit receives power, it applies a signal to the control input of the relay, so that the actuation control unit continues to receive power until that unit, or another control, interrupts power.

Using this arrangement, the supply of power to the actuation control unit and to the remainder of the patient handling system can be shut down completely during acquisition of magnetic resonance images to avoid RF emissions from this system.

These and other objects, features and advantages of the present invention will be more readily apparent from the detailed description of the preferred embodiments set forth below, taken in conjunction with the accompanying drawings.

BRIEF DESCRIPTION OF THE DRAWINGS

FIGS. 4 A-E are a series of perspective views of the assembly of the control kiosk of FIG. 3 in accordance with one aspect of the present invention;

DETAILED DESCRIPTION

Figure 3:
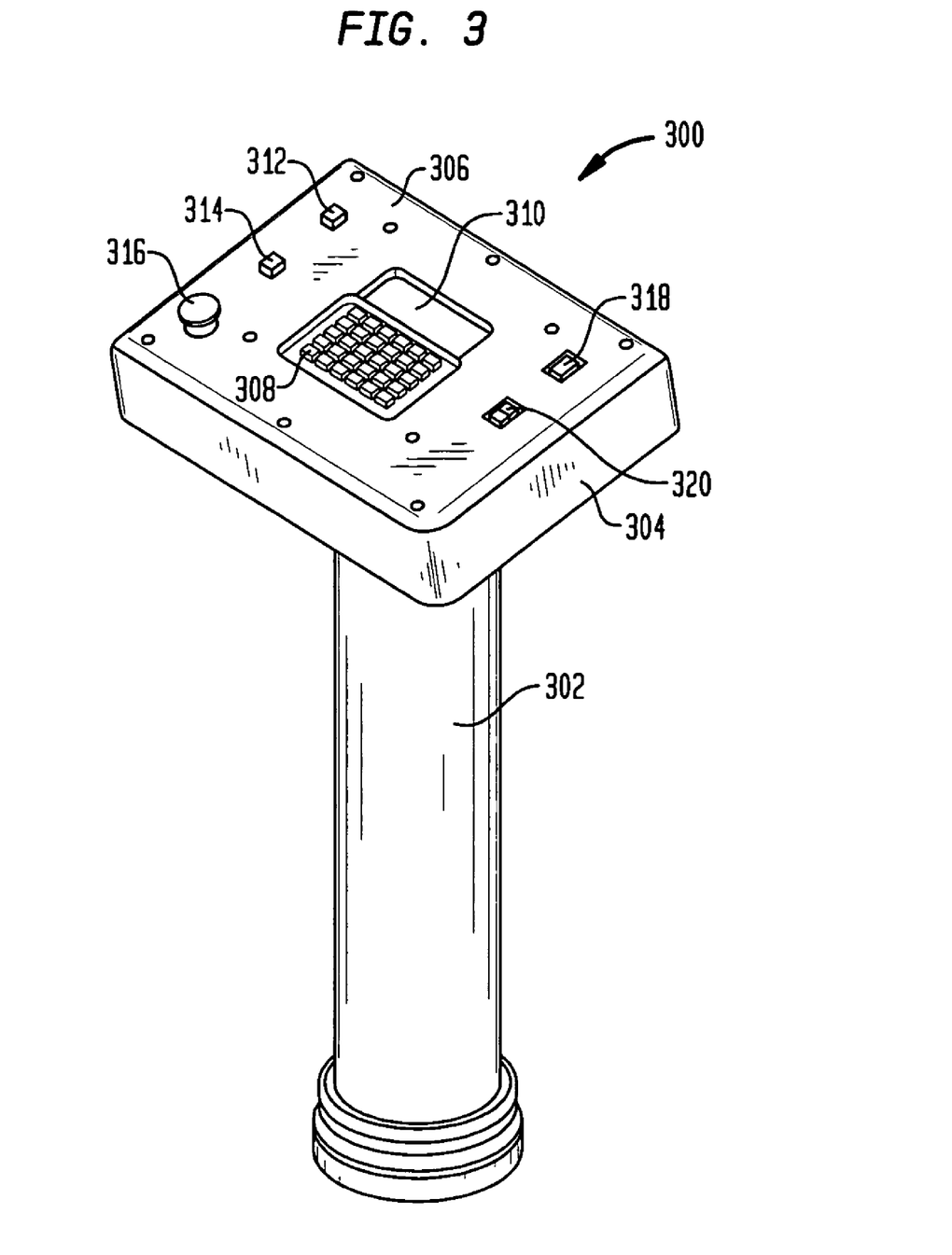
FIG. 3 is a perspective view of a control kiosk in accordance with one embodiment of the present invention.

FIG. 3 shows a control kiosk 300 which is used with a patient handling system such as patient handling system 106 in accordance with one embodiment of the present invention. Control kiosk 300 includes a support structure 302 and a control housing 304. The support structure 302 is hollow in order to house the power and data cables connecting the control housing 304 to the magnet subsystem 100. In a preferred embodiment, the support structure 302 is a tube. However, alternative embodiments include any structure capable of housing the requisite cables and capable of supporting the control housing 304. In a preferred embodiment, the support structure 302 is made of aluminum, which is advantageous in settings using MRI, as it is a non-magnetic material. However, alternative embodiments of the support structure may be manufactured of any non-magnetic material of sufficient strength, such as certain plastics. Furthermore, given the distance which the control kiosk 300 may be placed from the MRI magnet subsystem 100 and the relatively small amount of material involved in support structure 302, magnetic materials may be used. If the magnetic effect of the structure on the MRI magnet subsystem 100 is detectable and is constant, shimming of the MRI main magnet may be used to compensate for such effect.

Control housing 304 houses the electronics for the control interface. The control panel 306 mounted on control housing 304 has at least some of the controls 307, e.g., keyboard 308, buttons 312 and 314 as is further described herein below needed to operate at least some parts of the patient handling system 106. Preferably, the control panel 306 is inclined at an angle from the horizontal to facilitate ease of use.

The control and reconstruction computer which, among other functions, controls the operation of the magnet 102 and the flux generating means 104 as previously described, as well as the RF antennae, are typically housed in a room separate from the shielded room that houses the MRI magnet subsystem 100 and the control kiosk 300. Note, however, that control kiosk 300 may also be used to control the operation of the computer housed outside the shielded room.

In a preferred embodiment, the controls 307 on control panel 306 include a multi-function keyboard 308, an associated display 310, an on button 312, an off button 314, an emergency stop button 316, a home button 318, and a move button 320. In one embodiment, multi-function keyboard 308 and associated display 310 are located in the center of the control panel 306. The multifunction keyboard 308 may be backlit to enhance visibility in low light settings, as may be the associated display 310.

The on button 312, the off button 314, and the emergency stop button 316 may all be on one side of the control panel. The home button 318 and move button 320 may be on the opposite side of the control panel. The home button 318 returns the patient handling system 106 to a default position.

The move button 320 is a "dead-man switch." The stand-up patient handling system will only move when the move button is activated (depressed). The moment the button is not being activated, the stand-up patient handling system stops. Advantageously, such a move button 320 requires that an operator of the MRI apparatus remain present all through the patient position procedure, and prevents such an operator from walking away from patient positioning after programming the control kiosk 300. This enhances the safety and effectiveness of the patient positioning process.

Those skilled in the art will understand that the preferred embodiment described above for the controls 307 is only one embodiment among a wide variety of alternatives. In one alternative embodiment, all of the controls 307 could be implemented on a touch sensitive screen. The controls 307 would then be primarily software driven. Such a touch sensitive screen could be either a cathode ray tube (CRT) or a liquid crystal display (LCD). In another alternative embodiment, only a keyboard and display are used as controls 307.

Figure 4A:
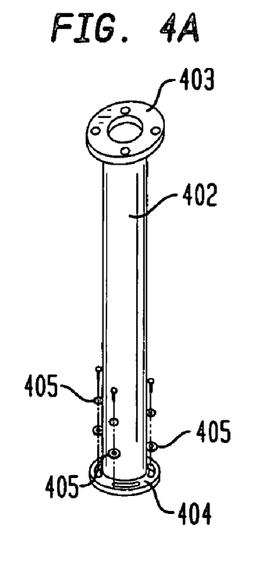
Figure 4B:
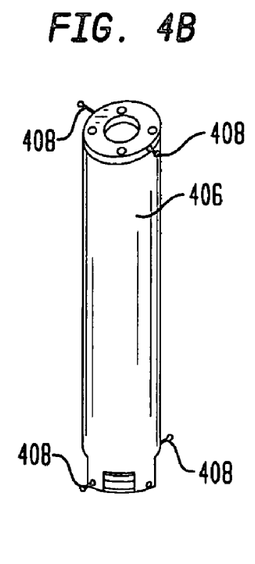
Figure 4C:
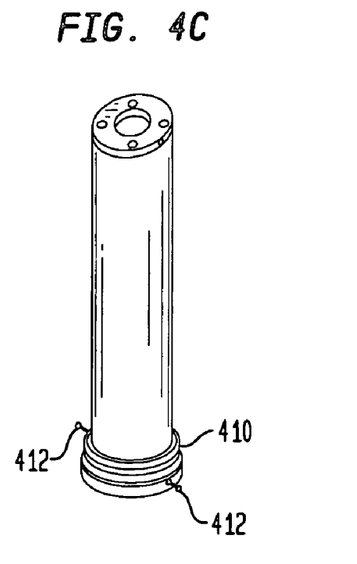
Figure 4D:
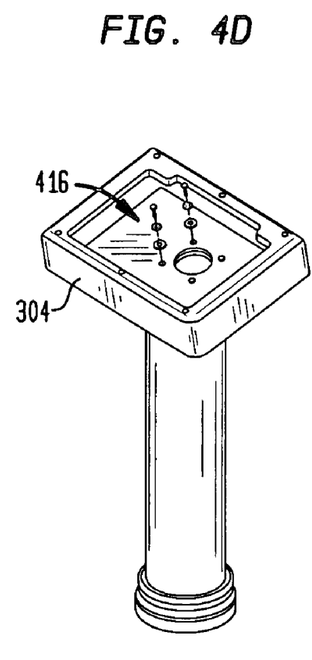
Figure 4E:
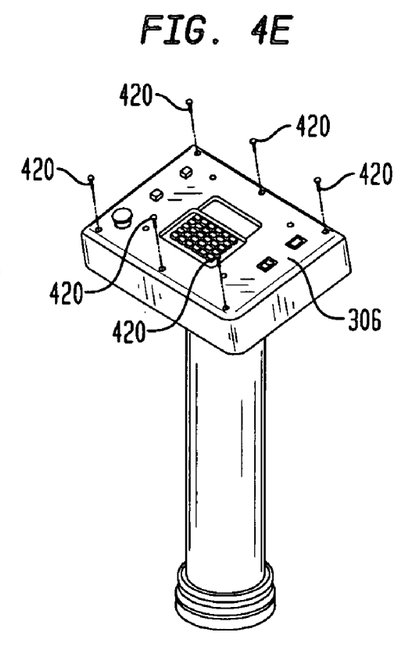

FIGS. 4A-4E show an illustrative example of the construction of the structural aspects of the control kiosk 300. FIG. 4A shows an inner tube 402 with upper flange 403 and lower flange 404 fastened to the ground with fasteners 405 through lower flange 404. FIG. 4B shows the attachment of an outer tube 406 to the inner tube 402 via fasteners 408. FIG. 4C shows a collar 410 being attached around the lower end of outer tube 406 and to lower flange 404 by fasteners 412. FIG. 4D shows the control housing 304 being mounted on upper flange 403 by fasteners 416. FIG. 4E shows the attachment of the control panel 306 to the control housing 304 by fasteners 420. Advantageously, the above illustrative example provides the hollow space in inner tube 402 for cables.

Figure 5:
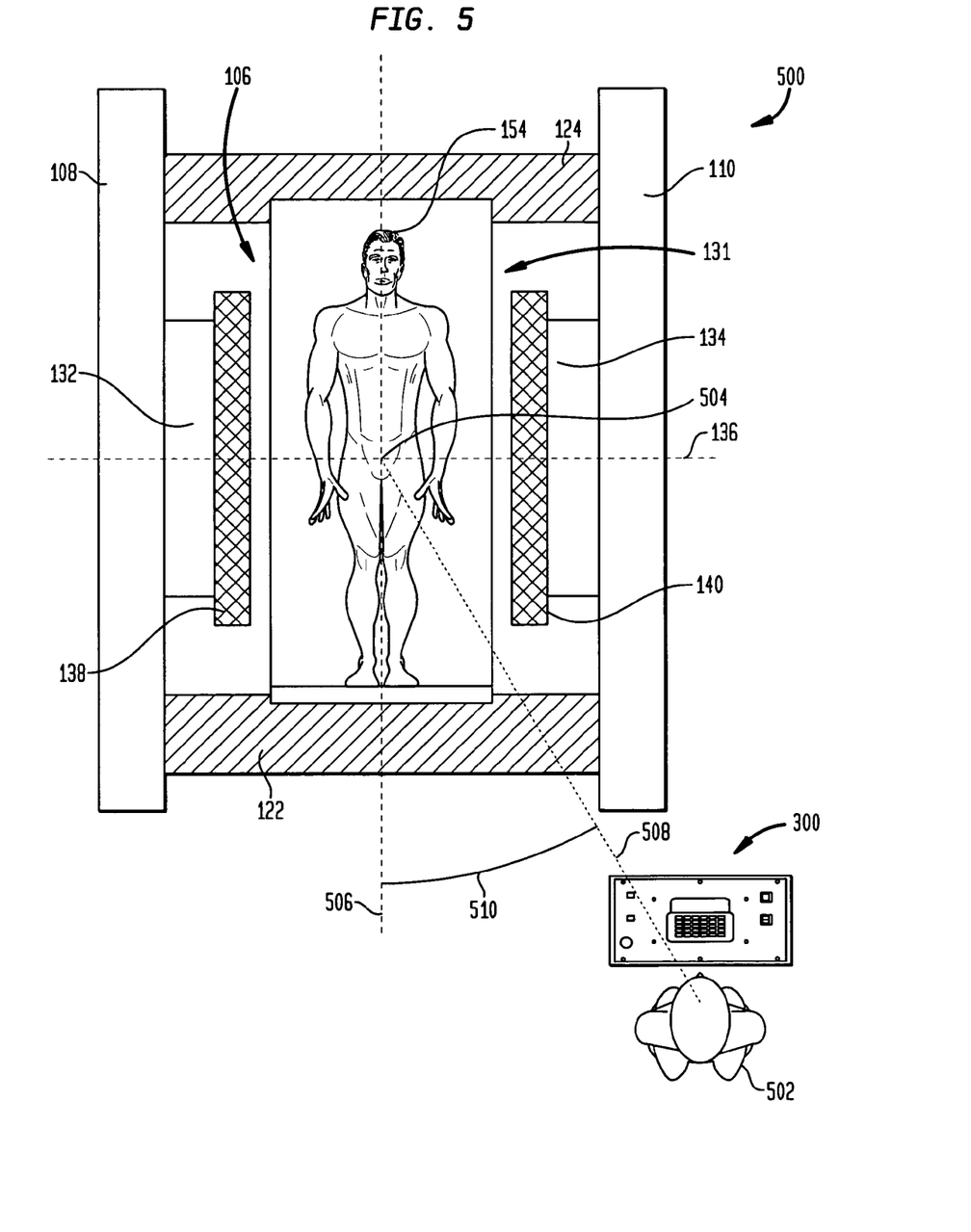
FIG. 5 is a diagrammatic top plan view of an MRI apparatus with the control kiosk of FIG. 3 in accordance with one aspect of the present invention.

One aspect of the present invention is the location of the control kiosk 300 with respect to the MRI magnet subsystem 100. Specifically, it is advantageous for the operator of an MRI apparatus 500 utilizing a patient handling system 106 such as in MRI magnet subsystem 100 to have as unobstructed a view as possible of the patient 154 during the positioning of the patient 154. FIG. 5 shows, for an MRI apparatus 500, a spatial relationship between the control kiosk 300 and the MRI magnet subsystem 100. An MRI apparatus such as the MRI apparatus 500 will include the MRI magnet subsystem 100 and the control kiosk 300, as well as the other common elements of a complete MRI apparatus, such as RF antennas, RF transmitter and receiver, and a control and reconstruction computer. The location of control kiosk 300 should place an MRI apparatus operator 502 with an angle of view which is not substantially blocked by the frame 102, but does not hinder loading patient 154 into patient handling system 106 through the front patient opening 125. The operator 502 should then have a view of patient 154 in the gap 131 between the magnetic poles 132 and 134. Preferably, a straight path may be left clear for loading patient 154, and sufficient room may be allowed for medical personnel to assist loading patient 154.

A center point 504 is a point defined by the intersection of the pole axis 136 and a median plane 506. The median plane 506 is the plane generally equidistant from the face of magnetic pole 112 and the face of second magnetic pole 114. A line of sight may be defined from the operator 502 to the center point 504. In FIG. 5, line of sight 508 is shown as an unbroken line from the operator 502 to the center point 504. The existence of an unobstructed or clear line of sight 508 demonstrates that the control kiosk 300 is in an acceptable position.

An angle 510 is defined between the median plane 506 and an unbroken line of sight 508. For any given magnet, there is a maximum value for angle 510. The maximum value for angle 510 defines a limit on the location of the control kiosk 300. The dimension of ferromagnetic frame 102 is a key determinant of the maximum angle 510 which allows an unbroken line of sight 508. Of course, if operator 502 can be at an angle less than maximum angle 510, his area of view may be increased.

Note that while the existence of an unbroken line of sight 508 from the operator 502 to the center point 506 may provide an acceptable view of the patient 154, it is not the only possible method of determining an acceptable location of the control kiosk 300. For example, a line of sight from an operator 502 to a point in the gap 131 other than the center point 506 may be used.

Figure 6:
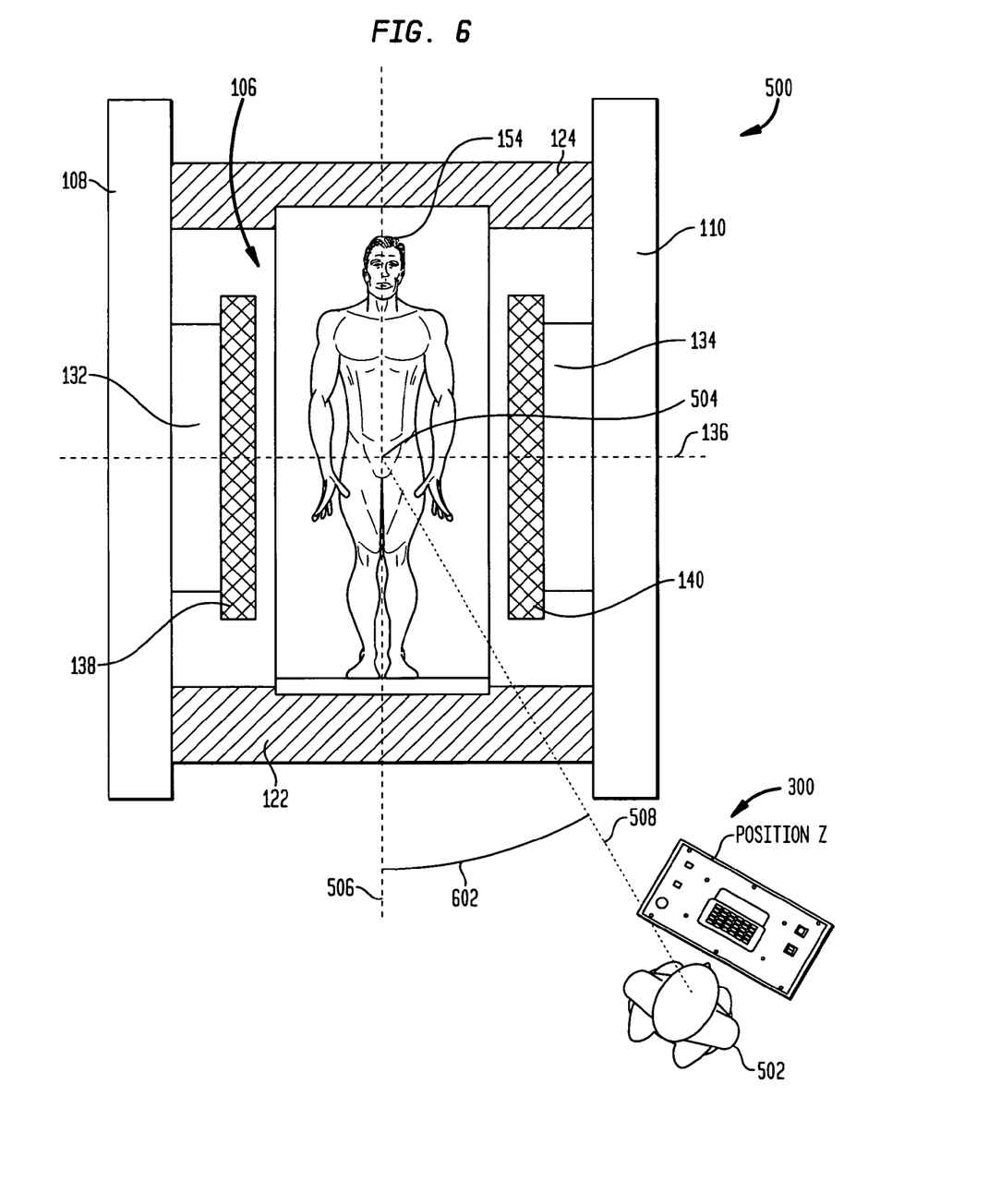
FIG. 6 is a diagrammatic top plan view of FIG. 5 with the control kiosk rotated.

In a preferred embodiment the control kiosk 300 rotates at least 45 degrees about a vertical axis. FIG. 6 illustrates this aspect of the present invention. FIG. 6 is identical to FIG. 5, except that control kiosk 300 has been rotated approximately 45 degrees to position Z. In this way, the operator's 502 path to the patient is not obstructed by the control kiosk 300. Thus, operator 502 no longer needs to walk around control kiosk 300 to get to the patient 154. Other possible advantages depend on the location of the control kiosk 300. One possible advantage of the ability to rotate the control kiosk 300 is to allow the operator 502 to change the origin of his line of sight to the center point 506. This may increase the area within the gap 131 the operator can view. In the illustrative embodiment shown in FIG. 6, the control kiosk 300 is in the same location as in FIG. 5. Therefore, a new angle 602 is subtended which is less than maximum angle 510. The operator 502 in FIG. 6 will enjoy a better field of view than the operator in FIG. 5. This aspect of the present invention allows more flexibility in the use of the control kiosk 300.

Alternatively, the rotation of control kiosk 300 may advantageously allow the operator 502 to continue operating or programming the control kiosk 300 while the patient 154 is being loaded into the patient handling system 106 by allowing the operator to move his body out of the straight approach to the gap 131. Again, in general the rotation of the control kiosk 300 allows more flexibility in its use.

The rotation of the control kiosk 300 may be achieved either by rotation of the control housing 304 with respect to the support structure 302, or the rotation of the support structure 302 with respect to collar 410. The result is equivalent.

Figure 7:
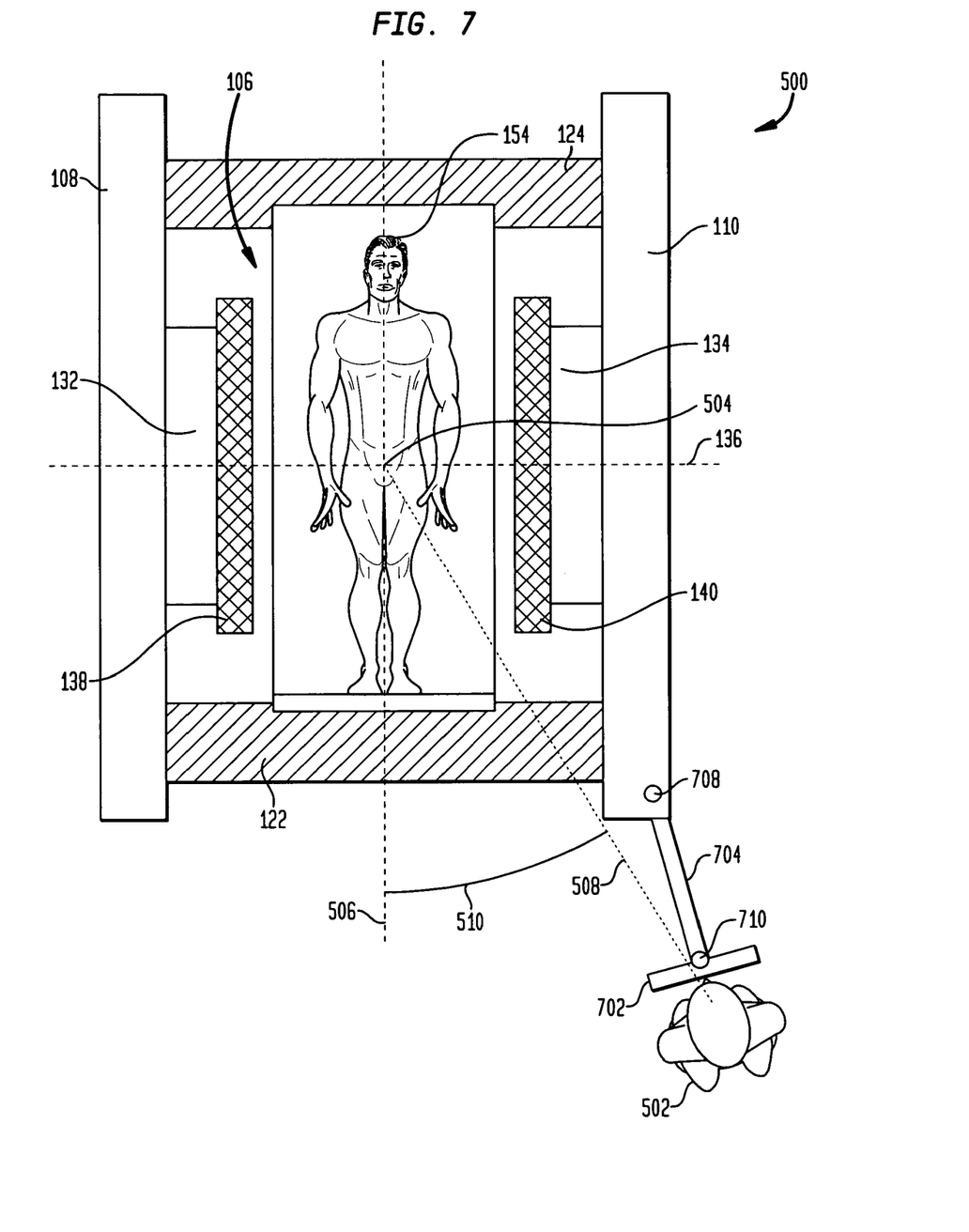
FIG. 7 is a diagrammatic top plan view similar to FIGS. 5 and 6 but depicting apparatus according to a further embodiment of the invention.

FIG. 7 shows an alternative embodiment where the controls 307 have been mounted on a control pad 702. For example, the control pad 702 might be a touch screen LCD. The control pad 702 is mounted on a swinging arm 704. The swinging arm 704 can be attached to any load bearing surface. In illustrative embodiment of FIG. 7, the swinging arm is mounted to the frame 102, specifically to side wall 110. The swinging arm can rotate about point 708 in the side wall 110, and the pad can pivot about point 710 on the swinging arm 704. Advantageously, such an embodiment of the present invention allows the controls 307 to be rotated, and also to be moved in space over a specified arc. This would increase the ability of the operator 502 to get out of the way of loading the patient 154 into the patient handling system 106, and then allow the operator to increase his field of view into gap 131 as needed. The flexibility of this embodiment can be further increased if the swinging arm 704 is also telescoping. Then, within the limits of the telescoping arm, any location could be achieved by the control 307 on control pad 702, and hence any location could be achieved by operator 502.

Figure 7A:
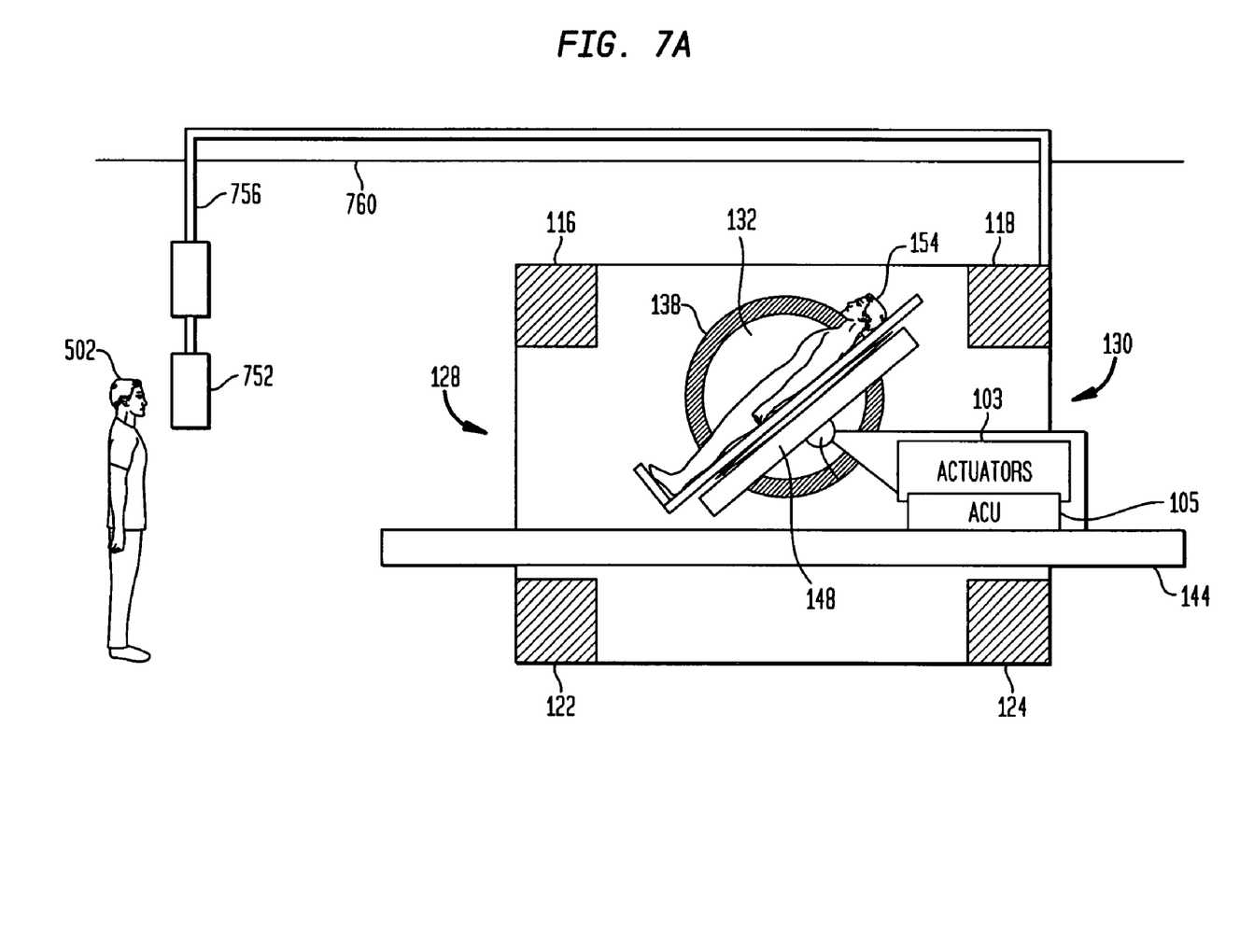
FIG. 7A is a diagrammatic side plan view in accordance with yet another embodiment of the present invention.

FIG. 7A shows a variant of the embodiment of FIG. 7. As FIG. 7A shows, the controls 307 are included on a control pad 752 which is mounted on a boom 756 extending down from a ceiling 760. The control pad 752 may include a touch screen display which allows an operator 502 access to the control pad 752. In accordance with this embodiment, the boom 756 may allow vertical adjustment of the control pad 752. In this way, the control pad 752 may be raised up out of the way as a patient is positioned in the patient-receiving space. Once the patient is positioned in the receiving space, the operator 502 then commences positioning of the region of interest in the imaging volume. Such positioning is accomplished in full view of the operator, as long as the operator 502 and control pad 752 are located within the maximum viewing angle.

Figure 8:
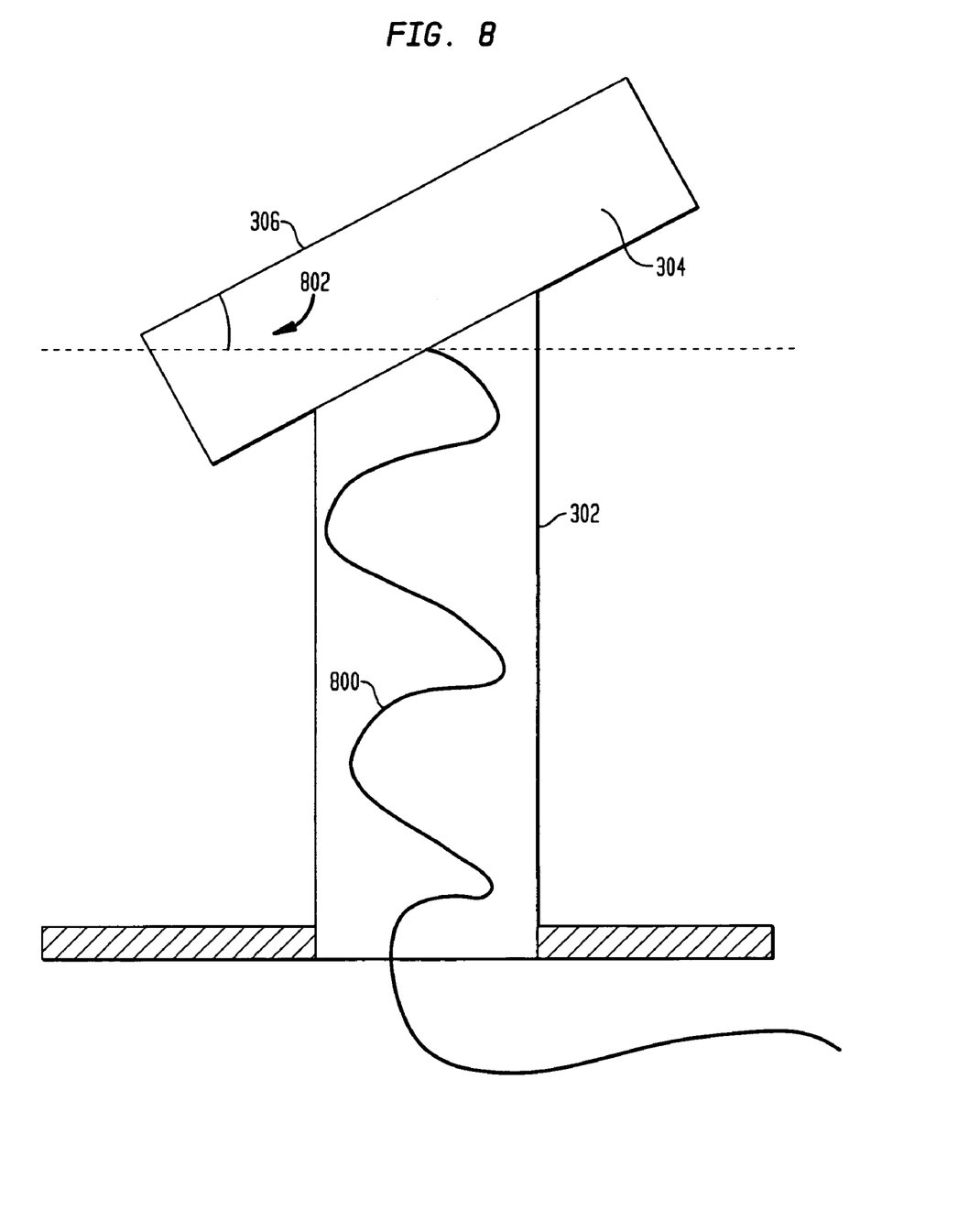
FIG. 8 is a diagrammatic sectional view of a control kiosk in accordance with one embodiment of the present invention.

FIG. 8 illustrates one embodiment of the present invention for achieving the rotation of the control kiosk 300. The support structure 302 contains within it cables 800. The cables 800 may include power cables and data cables of various types. The slack or coiling shown of cable 800 allows for twisting by the cables 800 when the control kiosk 300 or control housing 304 is rotated. FIG. 8 also illustrates that the control panel 306 is at an angle 802 from the horizontal plane to allow either use by operator 502.

Any number of variations are possible to allow either guided or free movement of a control kiosk 300 with respect the MRI magnet subsystem 100. In FIG. 7, a version of the control kiosk 300, the control pad 702, is mounted on a swinging arm 704. Other alternative for moving the control kiosk 300 or any other structure having the controls 307 include mounting on a track and mounting on a free moving wheeled carriage. The former embodiment could have the connecting cables run under the floor or across the floor. The latter embodiment would preferably run the cables over the floor. In yet another embodiment, the controls 307 could be mounted on a small handheld device, and connected by cable to the MRI magnet subsystem 100. This handheld device could be designed for two-handed or even one-handed operation.

The above alternative embodiments all teach the use of connecting cables such as data transmission cables and power transmission cables. However, data transmission could also be provided by free space or wireless data communication signals. Such by free space data communication signals may require line of sight from the controls 307 to the MRI magnet subsystem 100. An example of such line of sight signals is infrared signals. Free space data communication signals may also be non-directional in nature. RF waves and ultrasound are examples of such non-directional free space data communication signals. RF waves are less preferred due to the possibility of RF interference with the magnetic resonance imaging process.

When the control kiosk 300 is mobile, whether through the use of a pivotable or telescoping arm, a track, a wheeled carriage, or other means, it becomes possible to greatly improve the field of view the operator 502 has of the patient handling system 106. The mobile control kiosk is preferably moved out of the way during the loading of the patient 154. During this loading, a view of the patient handling system 106 by the operator 502 is not required, so the mobile control kiosk can be moved completely out of the way. During patient positioning, the operator 502 needs the best view of the patient handling system 106 possible, so preferably the mobile control kiosk is moved to the closest position possible to the median plane 506. Further, if possible, it is preferable that the mobile control kiosk be moved close to the center point 504, although not so close that the patient handling system 106 could strike the operator 504 or the mobile control kiosk. Thus a mobile control kiosk as seen in FIG. 7 and as described in the above alternative embodiments allows the field of view of the operator 504 to be optimized when needed, and allows the operator 504 to avoid interfering with patient loading when the operator is not needed.

In accordance with the present invention, the control kiosk 300 or control pads, 702 or 752, may be located in a room separate from the shielded room housing the MRI magnet subsystem 100. In such an arrangement, the operator responsible for positioning the patient within the patient-receiving space may be allowed to view the patient through a window. Such a window would, of course, have to provide a view within the maximum viewing angle. The operator may also be advantageously located directly in front of the patient in the patient-receiving space. Further, the control kiosk 300 or control pads, 752 or 702, may be co-located with the control and reconstruction computer.

As discussed above, the patient handling system is equipped with actuators 103 and actuation control unit 105 (FIG. 1) for moving the elements of the patient handling system. The actuation control unit, actuators and associated elements may be connected as seen in greater detail in FIG. 9. As discussed above, the actuation control unit preferably includes an electrical, electronic, electropneumatic, electrohydraulic or other control device which is at least partially operated by electricity. The actuation control unit includes an electrical power supply connection 902, which supplies electrical power to operate the internal elements of the control unit itself and which may also supply power to actuators 103 through the control unit. The actuation control unit also includes a power control output 904. The control unit 105 is configured or programmed to supply a signal such as a logic voltage signal as, for example, five volts at the power output connection 904 continually during operation of the control unit as further discussed below. The actuation control unit also includes one or more actuator control outputs 906 which are linked to actuators 103. The nature of these actuation control outputs will depend upon the structure of the actuators. For example, where the actuators include stepper motors, the actuation control outputs may include conventional stepper motor drive interfaces. Where the actuators include pneumatic or hydraulic components, the actuator control outputs may include electrical drive circuits for actuating solenoid operated or other electrically controlled pneumatic or hydraulic valves. With still other actuators, actuator control outputs 906 may take the form of non-electrical outputs such as optical, pneumatic, hydraulic or mechanical signal transmission devices.

Figure 9:
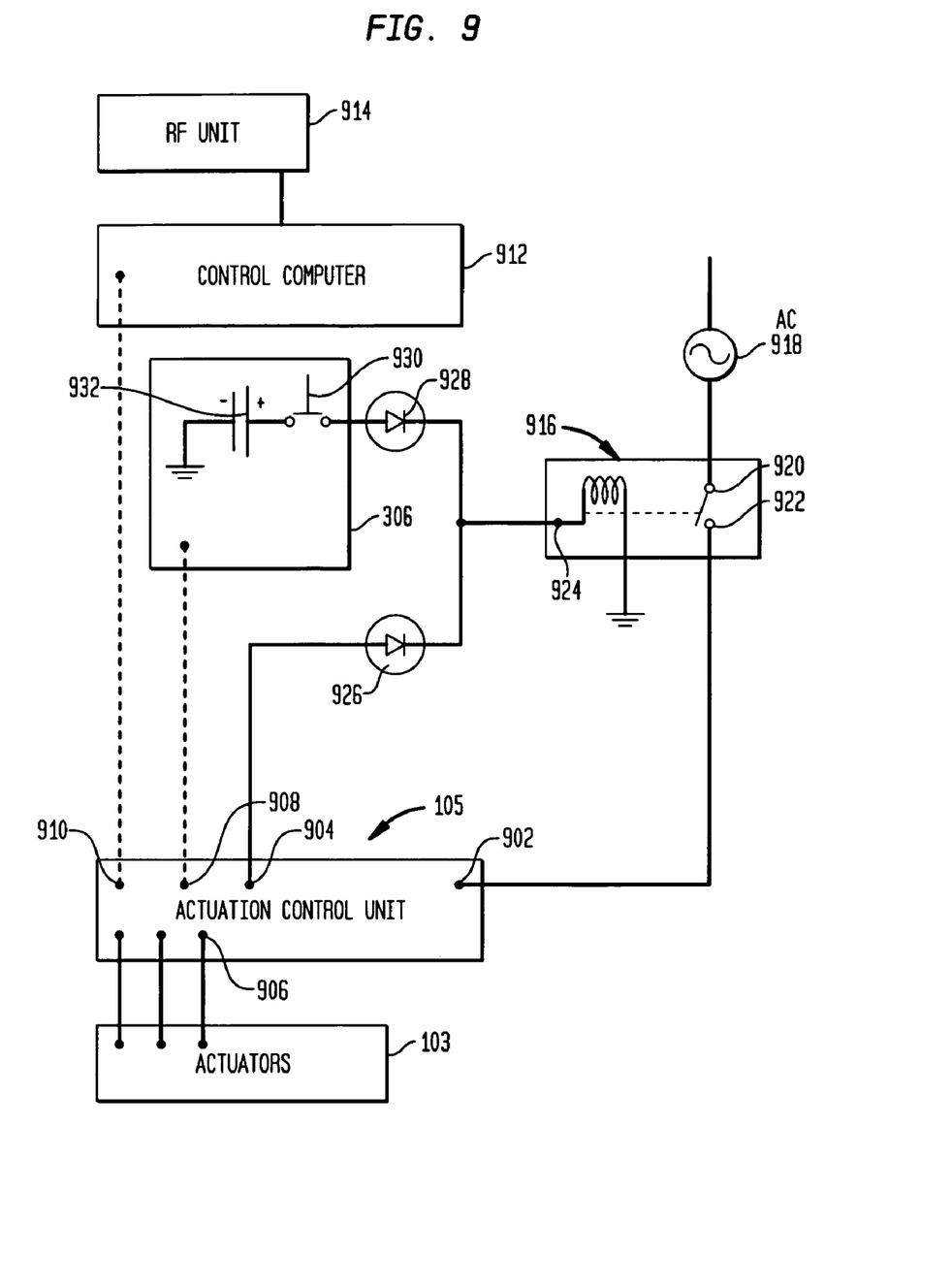
FIG. 9 is a schematic circuit diagram depicting portions of the apparatus shown in FIG. 1.

The actuation control unit also includes signal input/output ports 908 and 910. Signal port 908 is linked to control panel 306, whereas signal port 910 is linked to the control and reconstruction computer 912 of the system. While electrical power is supplied to actuation control unit 105, the actuation control unit responds to commands and instructions received from the control panel 306, from control and reconstruction computer 912, or both, through ports 908 and 910 to operate the actuators 103 by applying signals at actuator control outputs 906. Merely by way of example, in a purely manual scheme, the actuation control unit simply translates commands received from control panel 306 through port 908 into appropriate control signals at outputs 906. In a more sophisticated control scheme, the actuation control unit 105 may respond to commands received from control computer 912 to move the patient handling system in a particular manner to a predetermined position or sequence of positions, subject to manual overriding by commands entered through control panel 306.

The control and reconstruction computer 912 is linked to an RF unit 914. As is conventional in the magnetic resonance imaging art, the RF unit includes a radio frequency receiver and transmitter. The RF transmitter is arranged to apply radio frequency excitation signals to a patient disposed in the patient-receiving gap, whereas the RF receiver is arranged to receive the resulting magnetic resonance signals. The magnetic resonance signals are minuscule RF signals. Therefore, the RF receiver must be quite sensitive, and it is important to minimize or eliminate sources of spurious RF signals ("RF noise") in or near the patient-receiving gap. The electrical and electronic elements incorporated in the actuation control unit 105 and actuators 103 emit RF noise when these devices are receiving electrical power. Such RF noise emissions typically continue even if the actuation control unit is in a quiescent state, where it is merely waiting for additional commands and is not commanding the actuators to perform any function. Such RF noise can arise, for example, from operation of a digital component such as a microprocessor incorporating a clock or other circuit which operates continually while the unit is supplied with power.

As discussed above, the actuation control unit 105 and actuators 103 are located in proximity to the patient-receiving space or gap 131. In the embodiment illustrated in FIG. 9, the power supply connection 902 of the actuation control unit 105 is connected to a source of power 918 as, for example, a conventional power line through a relay 916. Relay 916 has a power input connection 920 connected to source 918, a power output connection 922 connected to the power source connection 902 of the actuation control unit 105, and a control input connection 924. Relay 916 is a normally open relay arranged to disconnect the power input 920 and power output 922 from one another when no control signal is applied to the control signal input 924 and to make the connection between input 920 and output 922 only while a control signal is applied at input 924. Although the relay is schematically depicted as an electromechanical relay in FIG. 9, other types of relays may be employed. For example, relay 916 may be a so-called "solid-state relay" incorporating one or more solid-state electronic devices such as transistors which can effectively connect and disconnect the power input and power output 922. Silicon control rectifiers may also be advantageously used for relay 916. Relay 916 desirably is located remote from the patient-receiving space or gap 131 of the magnet. For example, relay 916 desirably is positioned on the inside of an RF shielded enclosure (not shown) surrounding the magnet.

The control input 924 of relay 916 is connected to the power control output 904 of actuation control unit 105 through a diode 926. The control input 924 is also connected through another diode 928 to one terminal of a momentary switch 930. Switch 930 is positioned on control panel 306 of the aforementioned kiosk or in another location accessible to a human operator. Switch 930 may serve as the "on" switch 312 discussed above with reference to the control kiosk. The opposite terminal of switch 930 is connected to an auxiliary control power source 932, such as a battery or other power source capable of supplying a control signal-level voltage or current, as required to actuate relay 916. Diodes 928 are connected in an "or" configuration, so that a positive voltage applied at either switch 930 or output 926 will pass to input 924. However, a positive voltage applied at output 904 is blocked from switch 930 and vice-versa.

In operation, when the operator wishes to move the patient to a different position, he or she depresses switch 930. A signal voltage from source 932 passes to the control input 924 of relay 916. Relay 916 closes, thus connecting power input 920 to power output 922 and to the power source connection 902 of the actuation control unit. The actuation control unit responds to application of power by applying a signal at power control output 904. Typically, this signal at output 904 appears within a few seconds or tenths of seconds after power is applied at supply connection 902. For example, where the actuation control unit includes a microprocessor, the signal appears at power control output 904 as soon as the microprocessor completes its "power on" routine. This signal will also pass to the control input 924 of the relay, so that the relay will remain closed and actuation control unit 105 will remain in an operative state. Thus, the operator may release switch 930 as soon as this signal appears. Typically, the signal at output 904 appears so quickly that the operator can be instructed simply to depress switch 930 momentarily and then release it. A conventional signaling device such as an indicator lamp, audible signal device, or light-emitting diode may be connected to power control output 904 so as to provide a human-perceptible indication to the operator that the signal has appeared at output 904 and that it is, accordingly, safe to release switch 930.

In this condition, with power supplied to actuation control unit 105, the actuation control unit and actuators 103 will operate in response to other commands entered on control panel 306, or by control computer 912, or both to move the patient handling system and, thus, reposition the patient. The actuation control unit 105 is arranged to terminate the signal at power control output 904 once the patient handling system has reached the desired position, or when the operator or control computer commands the actuation control unit to turn off. For example, in a purely manual system, the actuation control unit may respond to a command from the "off" switch incorporated in control panel 306 to terminate the signal at output 904. The operator can provide this signal when the patient is in the desired position. Alternatively or additionally, the actuation control unit may respond to a signal from control computer 912 indicating that the patient is in the desired position. In another arrangement, the actuation control unit itself may determine that the desired position has been reached. For example, the actuation control unit may compare the actual position of the patient handling system to a desired position supplied from the control panel or from the control computer to determine whether the desired position has been reached, and may respond to such a determination by terminating the signal at power control output 904.

When the signal at power control output 904 ceases, relay 916 opens and power to power supply connection 902 is terminated. In this inoperative or "off" condition, the actuation control unit 105 and, hence, actuators 103 receive no electrical power and thus radiate no RF noise. The control computer 912 can operate the other elements of the magnetic resonance imaging system to acquire magnetic resonance information from the patient. The patient handling system 106 will be immobilized during these information acquisition steps. However, this is normally desirable, as it is normally desirable to acquire an image from a patient in a stationary condition. If it is desired to acquire information from the patient in a different position, the same sequence of steps can be repeated, using momentary switch 930 to turn the actuation control unit 105 on again. Once again, the actuation control unit begins to supply a signal from the power control output 904 as soon as it is turned on, so that relay 916 remains closed and the actuation control unit remains on until the patient is in the new desired position.

The features discussed above with reference to FIG. 9 can be varied in numerous ways. For example, where actuators 103 require electrical power in addition to that received through the actuator control outputs 906 of unit 105, such additional electrical power may be supplied through a connection (not shown) to the power output 922 of relay 916. In a further variant, more than one relay may be utilized as, for example, a first relay to supply power to the actuation control unit and a second relay (not shown) for supplying electrical power to the actuators themselves. The control inputs of these two relays may be connected in common, and this common connection may be connected to switch 930 and power control out 904 in the same way as control input 924 discussed above. Also, switch 930 need not be a directly operated manual switch. As discussed above, it is desirable to provide for control by a human operator for safety reasons. However, switch 930 may be actuated by control computer 912 or by another automated device. Also, switch 930 need not be a mechanical switch as shown; it may be a "solid-state switch" such as a transistor device. In a further variant, actuation control unit 105, or another device connected to the power output 922 of the relay, or a device connected to the control input 924 of the relay, may supply a signal to control computer 912 indicating that unit 105 is in the operative or "on" condition. The control computer can be arranged to inhibit acquisition of MRI images while this signal persists.

The features discussed above with reference to FIG. 9 are particularly useful with a positioning system such as that described with reference to FIG. 1, which is capable of placing a patient in numerous different positions. However, similar features can be used to operate a simple actuator for moving a patient in a single direction as, for example, in the system depicted above with reference to FIG. 2. Additional electrical devices useable in or near the patient-receiving space of the magnet may be connected to the power output 922 of the relay or the power output of another relay controlled in common with relay 916. Merely by way of example, the system may be equipped with devices for enhancing patient comfort, such as heating or cooling devices or entertainment units; monitoring devices such as cardiac or respiratory monitoring devices; or any other device which employs electric power. These devices will be activated and deactivated in the same manner as the actuation control unit and, accordingly, will not emit RF noise during the actual imaging procedures.

All of the features discussed above can be used in conjunction with magnets having elements other than ferromagnetic poles defining the patient-receiving space. For example, certain electromagnets have coils and do not have physical poles.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. Apparatus for magnetic resonance imaging comprising: an MRI magnet subsystem having a pair of pole faces; a patient handling system capable of three of axes of motion between said pair of pole faces, wherein said three axes of motion includes a substantially horizontal direction, a substantially vertical direction, and a rotation of said patient handling system; and a control kiosk spatially separate from said MRI subsystem and comprising a housing having first and second ends, said control kiosk being located in a room having a floor, the first end being supported by the floor and the second end having a control panel operable to control the motion of said patient handling system.

2. The apparatus of claim 1, further comprising one or more cables operationally connecting said control kiosk to said MRI magnet subsystem.

3. The apparatus of claim 2, wherein said one or more cables includes at least one data transmission cable or at least one data transmission cable and at least one power transmission cable.

4. The apparatus of claim 1, wherein said control kiosk is located such that an operator using said control kiosk can see said patient handling system.

5. The apparatus of claim 1, wherein said control kiosk is a touch-sensitive liquid crystal display.

6. A control kiosk spatially separate from a magnetic resonance imaging apparatus having a patient-receiving gap, said control kiosk comprising a support structure with a floor end, a floor collar and a top end and a control housing attached to said top end; and, wherein said control housing includes a control panel mounting controls for operating a patient handling system positioned within the patient-receiving gap and capable of three axes of motion, wherein said three axes of motion of said patient handling system includes a substantially horizontal direction, a substantially vertical direction, and a rotation of said patient handling system, and wherein said control housing can rotate with respect to said support structure.

7. The control kiosk of claim 6, wherein said floor collar attaches said floor end to the floor and wherein said control housing and said support structure rotate with respect to said floor collar.

8. The control kiosk of claim 6, wherein said support structure is a hollow tube.

9. The control kiosk of claim 6, wherein said support structure is made of a non-magnetic material.

10. The control kiosk of claim 9, wherein said support structure is made of aluminum.

11. The control kiosk of claim 6, wherein said controls mounted on said control panel include one or more elements selected from a group consisting of an on button and an off button, an emergency stop button, a home button for returning the patient handling system to a default position, and a movement button acting as a dead man's switch.

12. An apparatus for magnetic resonance imaging comprising:
an MRI magnet subsystem having a first magnetic pole with a generally flat face and a second magnetic pole with a generally flat face;
said first and second magnetic poles defining a gap between said faces of said first and second magnetic poles, a generally horizontal pole axis running through the center of said faces of said first and second magnetic poles and a median line at the height of said pole axis which is generally equidistant at all points from the faces of the first and second magnetic poles, and a center point at the intersection of said pole axis and said median line;
a patient handling system capable of three axes of motion provided within said gap; and
a control kiosk spatially separate from said MRI magnet subsystem, said control kiosk usable by an operator to control said patient handling system,
wherein said control kiosk is located such that the operator has an unobstructed line of sight defined from the operator to the center point.

13. The apparatus of claim 12, further comprising a structural connection between said MRI subsystem and said control kiosk.

14. The apparatus of claim 13, wherein said structural connection is a load-bearing arm capable of holding said control kiosk off the floor.

15. The apparatus of claim 14, wherein said load-bearing arm further includes a pivot attaching said load-bearing arm to said MRI subsystem allowing said load-bearing arm to swivel about said pivot.

16. The apparatus of claim 15, wherein said control kiosk is a touch sensitive liquid crystal display.

17. The apparatus of claim 13, wherein said structural connection is a ceiling boom capable of holding said control kiosk above the floor.

18. The apparatus of claim 17, wherein said control kiosk is a touch-sensitive liquid crystal display.

19. The apparatus of claim 13, wherein said structural connection comprises a member mounted to floor for supporting said control kiosk.

20. The apparatus of claim 19, wherein said member further includes a pivot and said control kiosk further includes a control housing, said pivot allowing said control housing to swivel about said member.

* * * * *

UNITED STATES PATENT AND TRADEMARK OFFICE
CERTIFICATE OF CORRECTION

PATENT NO. : 7,327,863 B1
APPLICATION NO. : 10/301187
DATED : February 5, 2008
INVENTOR(S) : Charles A. Green, Mark Gelbien and Joseph Citro It is certified that error appears in the above-identified patent and that said Letters Patent is hereby corrected as shown below:

Column 5, line 30, "a MRI" should read --an MRI--.
Column 13, line 46, "three of axes" should read --three axes--.
Column 13, line 60, "includes" should read --include--.
Column 14, line 10, "includes" should read --include--.
Column 15, line 7, "to floor" should read --to the floor--.

Signed and Sealed this

Seventh Day of April, 2009

JOHN DOLL
*Acting Director of the United States Patent and Trademark Office*